United States Patent [19]

Walker

[11] Patent Number: 4,600,538

[45] Date of Patent: Jul. 15, 1986

[54] CORTICOSTEROIDS FROM 17-KETO STEROIDS VIA 20-CYANO-$\Delta^{17(20)}$-PREGNANES

[75] Inventor: Jerry A. Walker, Oshtemo Township, Kalamazoo County, Mich.

[73] Assignee: The Upjohn Company, Kalamazoo, Mich.

[21] Appl. No.: 636,948

[22] Filed: Aug. 2, 1984

[51] Int. Cl.[4] ............................................. C07J 5/00
[52] U.S. Cl. ............................. 260/397.45; 260/397.5
[58] Field of Search ................................... 260/397.45

[56] References Cited

U.S. PATENT DOCUMENTS

| | | | |
|---|---|---|---|
| 4,041,055 | 8/1977 | Shephard et al. | 260/397.3 |
| 4,216,159 | 8/1980 | Hessler et al. | 260/397.1 |
| 4,342,702 | 8/1982 | Walker | 260/397.3 |
| 4,411,835 | 10/1983 | Walker | 260/397.45 |
| 4,500,461 | 2/1985 | Van Rheenen | 260/397.45 |

OTHER PUBLICATIONS

Synthesis, pp. 92–95 (1975) Academic Press, New York; Editor G. Schill et al.
J. Org. Chem. 43, 4374–4376 (1978) Side Chain Extension.
J. Org. Chem., 44, 702–710 (1979) R. W. Freerksen et al.
J. Am. Chem. Soc. 76, 5031–5034 (1954) G. I. Poos et al.
J. Am. Chem. Soc., 70, 1454–1458 (1948) L. M. Sarett.
J. Am. Chem. Soc. 71, 2443–2444 (1949) L. H. Sarett.
J. Am. Chem. Soc., 77, 196–198 (1955) P. R. Watson et al.
Helv. Chim. Acta 34, 359–372 (1951) Von J. Heer et al.

*Primary Examiner*—Elbert L. Roberts
*Attorney, Agent, or Firm*—Bruce Stein

[57] ABSTRACT

The process of the present invention transforms 17-keto steroids (I) to the corresponding corticoids (IV) in three steps.

18 Claims, No Drawings

CORTICOSTEROIDS FROM 17-KETO STEROIDS VIA 20-CYANO-$\Delta^{17(20)}$-PREGNANES

BACKGROUND OF THE INVENTION

The transformation of 17-keto steroids to corticoids is well known to those skilled in the art. Numerous routes have been utilized. See, for example, U.S. Pat. Nos. 4,041,055, 4,216,159, 4,342,702 and 4,411,835.

The addition of an α-nitrile anion to ketones has been reported, see Synthesis 92 (1975), including 17-keto steroids, see J. Org. Chem. 43, 4374 (1978). The J. Org. Chem. 43, 4374 (1978) publication discloses the addition of the lithiated mono anion of 3-unsubstituted propionitrile to a 17-keto steroid to give a 17β-hydroxy-17α-substituted steroid which upon dehydration with thionyl chloride gives a 20-cyano-$\Delta^{17(20)}$-steroid, however the oxidation of these 20-cyano-$^{17(20)}$ steroids to 17α-hydroxy 20-keto steroid does not work well, see J. Org. Chem. 44, 702 (1979). The -OR$_{21}$ substituent permits efficient oxidation of the 20-cyano-$\Delta^{17(20)}$-steroid (III) to the corticoid (IV). The addition of a β-mettalo-α-substituted propionitrile to a 17-keto steroid has not been reported. It is surprising and unexpected that the α-metallo-β-metalloxypropionitrile dianion (V) adds to the 17-keto steroid (I) without elimination of the -OR$_{21}$α substituent.

The oxidation of 21-acetoxy-$\Delta^{17(20)}$-20-cyanopregnanes to the corresponding 17,21-dihydroxy-20-keto steroid derivatives is well known in the steroid literature, see J. Am. Chem. Soc. 76, 5031 (1954); J. Am. Chem. Soc. 70, 1454 (1948); J. Am. Chem. Soc. 71, 2443 (1949); J. Am. Chem. Soc. 77, 196 (1955); Helv. Chim. Acta 34, 359 (1951); and J. Org. Chem. 44, 702 (1979).

The process of the present invention transforms the 17-keto steroid (I) starting materials to the corresponding corticoid (IV) products in only four steps.

SUMMARY OF THE INVENTION

Disclosed is a 17β-hydroxy steroid (II A-C).

Also disclosed is a process for the preparation of a C$_3$-protected 17β-hydroxy steroid (IIα) which comprises contacting a C$_3$-protected 17-keto steroid (I) with an α-metallo-β-metalloxypropionitrile (V) at a temperature of less than about 0°.

Further disclosed is a process for the preparation of a corticoid (IV) which comprises (1) contacting a C$_3$-protected 17-keto steroid (I) with an α-metallo-β-metalloxypropionitrile (V) to produce a 17β-hydroxy steroid (IIα), (2) contacting the 17β-hydroxy steroid (IIα) of step (1) with an acylating or silylating agent to produce a 21-hydroxy protected steroid (IIβ), (3) contacting the 21-hydroxy protected steroid (IIβ) of step (2) with a dehydrating agent to produce a $\Delta^{17(20)}$-20-cyano steroid (III) and (4) contacting the $\Delta^{17(20)}$-cyano steroid (III) of step (3) with an oxidizing agent.

DETAILED DESCRIPTION OF THE INVENTION

The 17-keto steroid (I) starting materials are well known to those skilled in the art or can readily be prepared from known compounds by methods well known to those skilled in the art. These include $\Delta^4$-3-keto (A), $\Delta^1$, $^4$-3-keto (B) and 3β-hydroxy-$\Delta^5$ (C) steroids, see Chart B. The 17-keto starting materials can be substituted at C$_6$, C$_9$, C$_{11}$ and/or C$_{16}$, with R$_6$, R$_9$, R$_{11}$ and R$_{16}$ as defined infra.

The A-ring of the 17-keto starting material must be protected, see, Protective Groups in Organic Synthesis, Theodora Greene, John Wiley & Sons, New York, 1981 and Steroid Reactions, Edited by Carl Djerassi, Holden-Day, San Francisco, 1962.

For the $\Delta^4$-3-keto steroids (A) the C$_3$ ketone is protected as the enol ether (Aa), ketal (Ab), or enamine (Ac) as is well known in the art, see Chart C. The preferred enol ether (Aa) is the methyl or ethyl ether. The preferred ketal (Ab) is the ethylene ketal. The preferred enamines are selected from the group consisting of pyrrolidino, morpholino and diethylaminoenamines. The enol ethers (a) are prepared by methods well known in the art, see J. Org. Chem. 26, 3925 (1961), Steroid Reactions, Edited by Carl Djerassi, Holden-Day, San Francisco, 1962, p 42–45, and U.S. Pat. No. 3,516,991 (Preparation 1). The ketals (b) are also prepared by well known methods, see Steroid Reactions, supra, p 11–14. The 3-enamines (c) are also prepared by methods well known in the art, see U.S. Pat. No. 3,629,298 and Steroid Reactions, supra, p 49–53.

The $\Delta^1$,$^4$-3-keto steroids (B) are protected as the 3-dialkylenamine (Ba) or ketal (Bb), see Chart C and U.S. Pat. Nos. 4,216,159 and 4,357,279.

The 3-hydroxy steroid (C) should have the 3β-hydroxyl group protected as the ether (Ca), see Chart C.

The C$_3$ protected forms (Aa, Ab and Ac) of the $\Delta^4$-3-keto steroids (A), the C$_3$ protected forms (Ba and Bb) of the $\Delta^1$, $^4$-3-keto steroids (B) and the C$_3$ protected form (Ca) of the 3β-hydroxy steroids (C) are considered equivalent to the non-protected or free form (A, B and C) respectively, since the C$_3$ protecting groups are readily removable to convert the C$_3$ protected forms (Aa, Ab, Ac, Ba, Bb and Ca) to the free or unprotected forms (A, B and C) respectively.

α-Metallo-β-metalloxy propionitrile (V), a dianion, can be prepared by treatment of 3-hydroxypropionitrile (HOCH$_2$CH$_2$CN) with a non-nucleophilic strong base in an aprotic solvent in a temperature range in which the dianion is stable. Suitable bases include lithium, sodium or potassium salts of disubstituted amines such as diisopropylamine, dicyclohexylamine, piperidine, diethylamine; bis(trialkylsilyl) amines such as hexamethyldisilazane and equivalents thereof. Suitable solvents include ethers such as THF, diglyme, ether; aromatic hydrocarbons such as benzene, toluene, xylene; hydrocarbons such as hexane, heptane, cyclohexane and mixtures thereof. The reaction temperature should be low, preferably less than about −20°, more preferably less than about −60°. The reaction should be performed under substantially anhydrous conditions in an aprotic solvent in the temperature range of about −20° to about −80°. About 2.1 equivalents of the base should be contacted at low temperature with the 3-hydroxypropionitrile. The α-metallo-β-metalloxy propionitrile dianion (V) is formed and kept under a nitrogen atmosphere under anhydrous conditions. The α-metallo-β-metalloxy propionitrile (V) is unstable at tempertures above about −20°. It is preferred to prepare 2.1 equivalents of lithium diisopropylamide from diisopropylamine and n-butyllithium in THF/hexane at about −40°; the 3-hydroxypropionitrile is then added to the lithium diisopropylamide at about −60° to prepare the α-metallo-β-metalloxy propionitrile (V). The preferred α-metallo-β-metalloxy propionitrile is the dilithio-3-hydroxypropionitrile, α-lithio-β-lithioxypropionitrile.

The C$_3$ protected 17-keto steroid (I) is reacted with the α-metallo-β-metalloxy propionitrile (V) to produce the C$_3$ protected 17β-hydroxy steroid (IIα).

The C$_3$ protected 17-keto steroid (I) is reacted with the α-metallo-β-metalloxy propionitrile (V) at about −20° to about −80° under anhydrous conditions. The C$_3$ protected 17-keto steroid is preferably added in solution or in a solvent in which it is at least partially soluble. The reaction is allowed to proceed until judged complete by TLC. The reaction mixture can be warmed once the reactants have been mixed. An excess of the α-metallo-β-metalloxy propionitrile (V) is usually advantageous but is not necessary. Once the reaction is complete the 17β-hydroxy-steroid (IIα) is isolated by means well known to those skilled in the art, the addition of water and/or a dilute acid followed by extraction of the product into an organic solvent to remove the inorganic salts. The C$_3$-protected A-ring can have the protecting groups removed in situ if so desired by means well known to those skilled in the art i.e. an enol ether (Aa) can be removed with aqueous acid. The reaction upon workup produces the 17β-hydroxy steroid (IIα) where R$_{21α}$ is a hydrogen atom.

The C$_3$ protecting group can be removed from the C$_3$ protected (Aa, Ab, Ac, Ba, Bb or Ca) 17β-hydroxy steroid (IIα) to produce the 17β-hydroxy steroid (IIα) in its free or not protected form (A-C). If the C$_3$ protecting group is left on at this stage it can be removed later.

The 21-hydroxyl group (R$_{21α}$ is a hydrogen atom) is selectively protected as an acyl or silyl derivative, preferably as an acyl derivative to give the 21-hydroxy protected steroid (IIα).

The addition of the C$_{21}$ protecting group is accomplished by standard procedures; for example, acylation with acetic anhydride and pyridine; silylation with trimethylsilyl chloride as is well known to those skilled in the art. Regarding the acylation using acetic anhydride and pyridine is preferred to treat the 17β-hydroxy steroid (IIα) and pyridine with a slight excess of acetic anhydride under mild conditions to give the 17β-hydroxy 21-acetate (IIα). Other acylating agents can be used such as acetyl chloride, a mixed anhydride of acetic acid etc. Other acyl groups (-CO-R$_{21}'$) include C$_2$ to C$_6$ or phenyl. The 21-hydroxy protected steroid (IIα) can be isolated by standard methods well known to those skilled in the art or can be treated in situ with a dehydrating agent to give the Δ$^{17(20)}$-20-cyano steroid (III).

The 21-hydroxy protected steroid (IIβ) is transformed to the corresponding Δ$^{17(20)}$-20-cyano steroid (III) by reaction with a dehydrating agent. Dehydrating agents such as thionyl chloride, phosphorous oxychloride or chlorosulfonic acid can be used to give the Δ$^{17(20)}$-20-cyano steroid (III). This is a similar reaction as to that reported J. Org. Chem. 43, 4374 (1978). The reaction with thionylchloride is best accomplished by addition of a slight excess of thionyl chloride at less than 0° preferably about −15°. Thionyl chloride is the preferred dehydrating agent. The mixture is then warmed to 0° and quenched with water. The Δ$^{17(20)}$-20-cyano steroid (III) can be isolated by means well known to those skilled in the art, —by extraction of the product into an organic solvent with removal of the inorganics and pyridine by aqueous washes. The product can be crystallized from the organic solvent to give the desired Δ$^{17}$ $^{(20)}$-20-cyano steroid (III).

The Δ$^{17(20)}$-20-cyano steroid (III) is transformed to the corticoid (IV) by reaction with an oxidizing agent as is well known to those skilled in the art, see J. Am. Chem. Soc. 76, 5031 (1954); J. Am. Chem. Soc. 70, 1454 (1948); J. Am. Chem Soc. 71, 2443 (1949); J. Am. Chem. Soc. 77, 196 (1955); Helv. Chem. Acta 34, 359 (1951); and J. Org. Chem. 44, 702 (1979). Suitable oxidizing agents include potassium permanganate, osmium tetroxide.

The use of potassium permanganate is preferred. In this case the Δ$^4$, 3-keto (A) ring system must be protected, preferably as the ethylene ketal. In the first step, if the C$_3$ protecting group is an enol ether (Aa), the 17β-hydroxy steroid (II) will be the enol ether (Aa). The 17β-hydroxy steroid enol ether (IIAa) can be converted to the C$_3$ ethylene glycol protecting group by reacting the 17β-hydroxy enol ether (IIAa) with ethylene glycol and acid. The Δ$^4$, 3-keto (A) ring system is then regenerated from the ethylene ketal by acidic hydrolysis as is well known to those skilled in the art, see J. Am. Chem. Soc. 76, 5031 (1954).

The corticoid (IV) products are useful as is well known to those skilled in the art.

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

THP refers to tetrahydropyranyl.

EEE refers to ethoxy ethyl ether [—O—CH(CH$_3$)OCH$_2$CH$_3$].

p-TSA refers to p-toluenesulfonic acid monohydrate.

TEA refers to triethylamine.

NMR refers to nuclear (proton) magnetic resonance spectroscopy, chemical shifts are reported in ppm (δ) downfield from tetramethylsilane.

TMS refers to trimethylsilyl.

When solvent pairs are sued, the ratios of solvents used are volume/volume (v/v).

Ether refers to diethyl ether.

Androstenedione refers to androst-4-ene-3,17-dione.

M is a lithium, sodium or potassium ion.

M' is a lithium, sodium or potassium ion.

R is alkyl of 1 thru 6 carbon atoms or phenyl.

R' is alkyl of 1 thru 6 carbon atoms or phenyl.

R'' is alkyl of 1 thru 6 carbon atoms or phenyl.

R$_3$ is an alkyl group of 1 thru 5 carbon atoms, with the proviso that with the ketal (Ab, or Bb) and the enamine (Ac and Ba) the R$_3$ groups can be the same or different and can be connected and with the enamine (Ac and Ba) if cyclized the ring can contain hetero atoms.

R$_3'$ is an alkyl group of 1 thru 3 carbon atoms or a TMS, THP or EEE group.

R$_6$ is a hydrogen or fluorine atom or methyl group.

R$_9$ is nothing, a hydrogen, fluorine or oxygen atom which makes the C ring
  (a) Δ$^{9(11)}$ when R$_9$ is nothing and
  (b) 9β,11β-epoxide when R$_9$ and R$_{11}$ taken together are an oxygen atom.

R$_{11}$ is a hydrogen or oxygen atom, two hydrogen atoms, or α- or β-hydroxyl group which makes the C-ring
  (a) Δ$^{9(11)}$ when R$_{11}$ is a hydrogen atom,
  (b) 9β,11β-epoxide when R$_9$ and R$_{11}$ taken together are an oxygen atom and between C$_{11}$ and R$_{11}$ is a single bond, and (c) a ketone when $R_{11}$ is an oxygen atom and ⋯ between $C_{11}$ and $R_{11}$ is a double bond.

$R_{16}$ is a hydrogen atom or methyl group.

$R_{21}$ is a hydrogen atom, —CO—$R_{21}'$, —SiRR'R" or M';

$R_{21}'$ is an alkyl group of 1 thru 5 carbon atoms or phenyl.

$R_{21}\alpha$ is a hydrogen atom or M'.

$R_{21}\beta$ is a —CO—$R_{21}'$ or —SiRR'R" group.

X is a hydrogen atom or nothing, when X is nothing the ⋯ between XO and $C_3$ is a double bond and when X is a hydrogen atom the ⋯ between the XO and $C_3$ is a single bond.

~ indicates that the attached group can be in either the α of β configuration.

⋯ is a single or double bond.

When the term "alkyl of _ through _ carbon atoms" is used, it means and includes isomers thereof where such exist.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

17β-Hydroxy-17α-(2-hydroxy-1-cyanoethyl)androsta-4,9(11)-dien-3-one (II A)

Dry THF (300 ml) and distilled diisopropylamine (30 ml) are mixed and cooled to less than −50°. Over a period of 10 minutes n-butyl lithium and hexane (1.6 N, 125 ml) are added by an addition funnel. After 30 minutes at less than −40°, 3-hydroxypropionitrile (6.55 g, 63 ml) is added dropwise. The resulting mixture is brought to −40° over 15 minutes, than cooled back down to less than −65°. After a total time of 1 hour, 3-hydroxyandrosta-3,5,9(11)-trien-17-one 3-methyl enol ether (I Aa) is added as a solid in one portion. The resulting slurry is stirred at less than −65° for 2 hours, then slowly over a period of 1 hour, brought to 5°. A solution of saturated aqueous ammonium chloride (75 ml) is added and the two-phase mixture is brought to 20°–25°. The layers are separated and the aqueous layer is extracted with methylene chloride (2×150 ml). The organic extracts are combined and back-washed with water (2×150 ml) and concentrated under reduced pressure to give a semi-solid. The semi-solid material is slurried in methylene chloride (100 ml). The solids are isolated and washed with additional methylene chloride. The solid material is suspended in methylene chloride (100 ml) and treated with aqueous hydrochloric acid (6 N, 10 drops) at 20°–25°. The mixture is stirred for 24 hours during which time most of the solids dissolved. The resulting mixture is diluted with methylene chloride (150 ml), extracted with water (100 ml) and concentrated under reduced pressure to give a solid. The solid is triturated with ethyl acetate (100 ml) at 20°–25° for 16 hours and re-isolated to give the title compound. NMR (CDCl$_3$) 0.97, 1.37, 2.23, 3.32, 3.43, 4.17, 5.60 and 5.73 δ.

EXAMPLE 2

17β-Hydroxy-17α-(2-acetoxy-1-cyanoethyl)androsta-4,9(11)-dien-3-one (II A)

17β-Hydroxy-17α-(2-hydroxy-1-cyanoethyl)androsta-4,9(11)-dien-3-one (II A, Example 1, 3.55 g), dry pyridine (30 ml), acetic anhydride (1.23 ml) are stirred at 20°–25° for 18 hours, then poured into water (250 ml) and methylene chloride (150 ml). The layers are separated and the aqueous layer is extracted with methylene chloride (60 ml). The organic layers are combined, washed with aqueous hydrochloric acid (1 N, 100 ml), dried over sodium sulfate and concentrated under reduced pressure to give the title compound. NMR (CDCl$_3$) 0.98, 1.37, 2.13, 3.02, 3.18. 4.50, 5.60 and 5.75 δ.

EXAMPLE 3

20-Cyano-21-hydroxypregna-4,9(11),17(20)-trien-3-one 21-acetate (III A)

17β-Hydroxy-17α-(2-acetoxy-1-cyanoethyl)androsta-4,9(11)-dien-3-one (II A, Example 2) is dissolved in pyridine (30 ml) and the mixture cooled to less than −50° under nitrogen. Thionyl chloride (0.86 ml) is added dropwise. After 30 minutes the mixture is brought to 0° and treated with water (10 ml). The mixture is transferred to a separatory funnel with methylene chloride (100 ml) and water (250 ml). The aqueous layer is separated and extracted with methylene chloride (2×50 ml). The organic phases are combined and washed with aqueous hydrochloric acid (0.5 N, 100 ml), dried over sodium sulfate and concentrated under reduced pressure to a solid. The solid is recrystallized from ethyl acetate to give the title compound. NMR (CDCl$_3$) 0.98, 1.37, 2.12, 4.62, 5.57 and 5.73 δ.

Example 4

20-Cyano-21-hydroxypregna-4,9(11),17(20)-trien-3-one 21-acetate 3-ethylene glycol ketal (III A)

20-Cyano-21-hydroxypregna-4,9(11),17(20)-trien-3-one 21-acetate (III A, Example 3, 70 ml), methylene chloride (2 ml), ethylene glycol (0.12 ml) and trimethylorthoformate (0.05 ml) are stirred at 20°–25°. p-TSA (3 mg) is added. After 1.5 hours at 20°–25° triethylamine (5 drops) is added and the solvent removed under reduced pressure to give the crude ketal as a mixture of Δ$^4$ and Δ$^5$-isomers of the title compound.

EXAMPLE 5

17α-21-Dihydroxypregna-4,9(11)-diene-3,20-dione 21-acetate (IV A)

The ketal mixture of Example 4 is dissolved in dry acetone (2 ml) and ethylene glycol (0.6 ml). The mixture is cooled to 0°–5° and with stirring under nitrogen atmosphere potassium permanganate (80 ml) is added as a solid powder. After 4 hours aqueous sodium bisulfite (1.5 ml) is added followed by ethyl acetate (10 ml), water (5 ml) and formic acid (88%, 20 microliters). After approximately 30 minutes the layers are separated and the aqueous layer is extracted with ethyl acetate (2×10 ml). The organic phases are combined, washed with aqueous sodium sulfate (5 ml), dried over sodium sulfate and concentrated under reduced pressure to give a crude crystalline product.

The crude crystalline product is dissolved in acetone (5 ml) and treated with p-TSA (10 mg) at reflux for 2 hours. On cooling the mixture is diluted with water (10 ml) which gives a precipitate which is isolated and dried under reduced pressure to give the title compound. NMR (CDCl₃) 0.64, 1.33, 2.18, 4.97, 5.56 and 5.75 δ.
CHART A
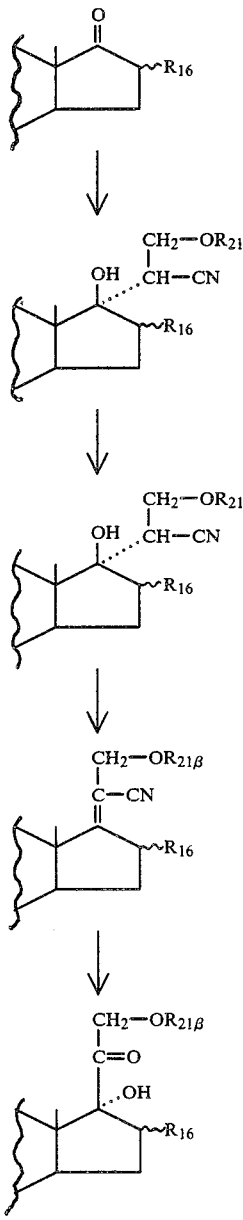
CHART B
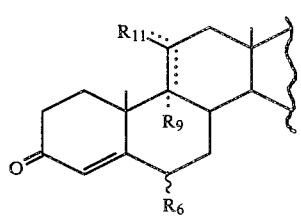
(A)
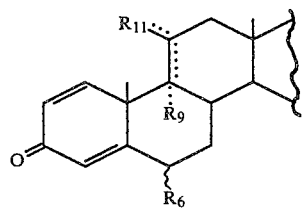
(B)
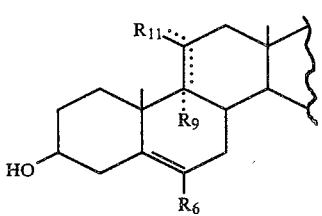
(C)
CHART C
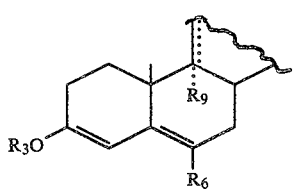
(Aa)
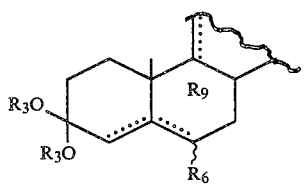
(Ab)
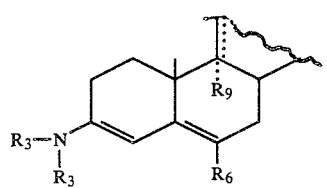
(Ac)
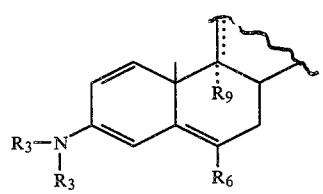
(Ba)
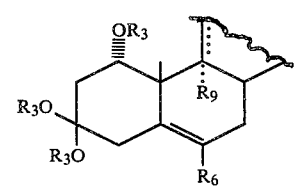
(Bb)

-continued
CHART C

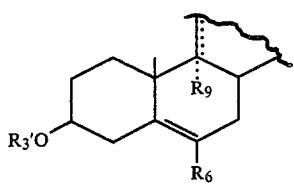
(Ca)

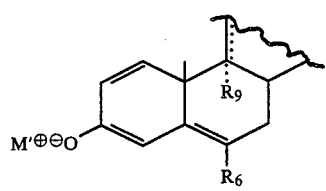
(Bc)

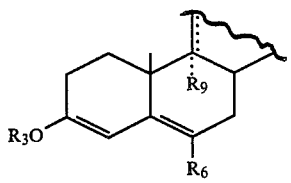
(Aa)

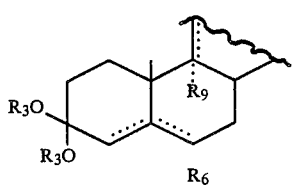
(Ab)

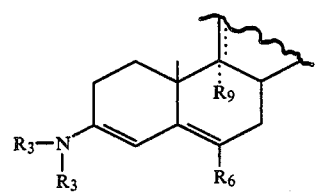
(Ac)

I claim:
1. A 17β-hydroxy-steroid of the formula

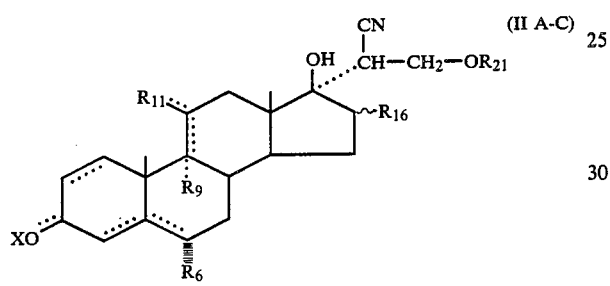
(II A-C)

and C$_3$ protected forms thereof where
X is a hydrogen atom or nothing; when X is nothing the ⁓ between XO and C$_3$ is a double bond, when X is a hydrogen atom the ⁓ between XO and C$_3$ is a single bond;
R is alkyl of 1 thru 6 carbon atoms or phenyl;
R' is alkyl of 1 thru 6 carbon atoms or phenyl;
R" is alkyl of 1 thru 6 carbon atoms or phenyl;
R$_6$ is a hydrogen or fluorine atom or methyl group;
R$_9$ is nothing, a hydrogen, fluorine or oxygen atom which makes the C ring
  (a) $\Delta^{9(11)}$ when R$_9$ is nothing and
  (b) 9β,11β-epoxide when R$_9$ and R$_{11}$ taken together are an oxygen atom;
R$_{11}$ is a hydrogen or oxygen atom, two hydrogen atoms, or α- or β-hydroxyl group which makes the C-ring
  (a) $\Delta^{9(11)}$ when R$_{11}$ is a hydrogen atom,
  (b) 9β,11β-epoxide when R$_9$ and R$_{11}$ taken together are an oxygen atom and ⁓ between C$_{11}$ and R$_{11}$ is a single bond, and
  (c) a ketone when R$_{11}$ is an oxygen atom and ⁓ between C$_{11}$ and R$_{11}$ is a double bond;
R$_{16}$ is a hydrogen atom or methyl group;
R$_{21}$ is a hydrogen atom, —CO—R$_{21}'$, —SiRR'R" or M';
R$_{21}'$ is alkyl of 1 thru 5 carbon atoms or phenyl;
⁓ indicates that the attached group can be in either the α or β configuration;
⁓ is a single or double bond;
M' is a lithium, sodium or potassium ion
where the Δ$^4$-3-keto 17β-hydroxy steroid (II A) is in the C$_3$ protected form where R$_3$ is alkyl of 1 thru 5 carbon atoms with the proviso that with the detal (Ab) and the enamine (Ac), the R$_3$ groups can be the same or different and can be connected and with the enamine (Ac) is cyclized the ring can contain hetero atoms
where the Δ$^{1,4}$-3-keto 17β-hydroxy steroid (II B) is in the C$_3$ protected form

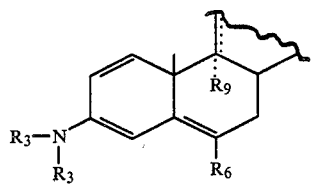
(Ba)

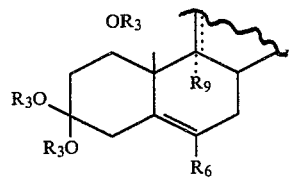
(Bb)

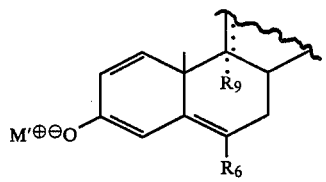
(Bc)

2. A 17β-hydroxy steroid according to claim 1 where the 17β-hydroxy steroid (II) is a Δ$^4$-3-keto 17β-hydroxy steroid of the formula

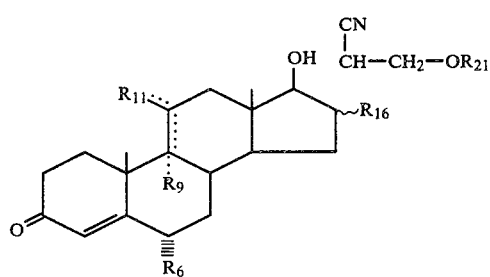

where $R_6$, $R_9$, $R_{11}$, $R_{16}$, $R_{21}$, $\sim$, and $⋮⋮$ are defined in claim 1.

3. A 17β-hydroxy steroid according to claim 1 where the 17β-hydroxy steroid (II) is a $\Delta^{1,4}$-3-keto 17β-hydroxy steroid of the formula

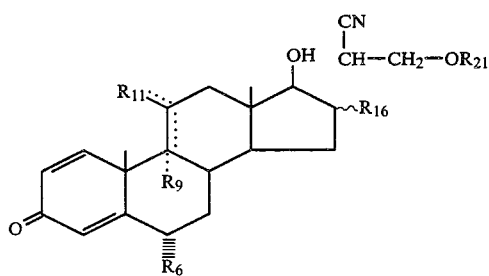

where $R_6$, $R_9$, $R_{11}$, $R_{16}$, $R_{21}$, $\sim$, and ___ are defined in claim 1.

4. A 17β-hydroxy steroid according to claim 1 where $R_9$ is nothing or an oxygen atom and where $R_{11}$ is a hydrogen atom or an oxygen atom making the C-ring $\Delta^{9(11)}$ or an 9β,11β-epoxide.

5. A 17β-hydroxy steroid according to claim 1 where $R_{21}$ is selected from the group consisting of hydrogen atom, —CO—CH$_3$, —CO—C$_2$H$_5$, —So(CH$_3$)$_3$, or —Si(CH$_3$)$_2$C(CH$_3$)$_3$.

6. A 17β-hydroxy steroid according to claim 1 which is selected from the group consisting of 17β-hydroxy-17α-(2-hydroxy-1-cyanoethyl)androstoa-4,9(11)-dien-3-one and 17β-hydroxy-17α-(2-acetoxy-1-cyanoethyl)androsta-4,9(11)-dien-3-one.

7. A process for the preparation of a C$_3$-protected 17β-hydroxy-steroid of the formula

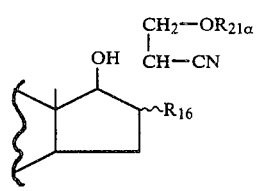

which comprises contacting a C$_3$-protected 17-keto steroid of the formula

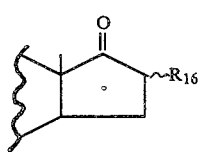

with an α-metallo-β-metalloxypropionitrile of the formula

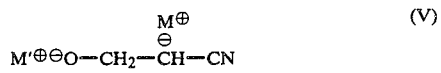

at a temperature of less than about 0° where
$R_{16}$ is a hydrogen atom or methyl group;
$R_{21}\alpha$ is a hydrogen atom, or M';
M is a lithium, sodium or potassium ion;
M' is a lithium, sodium or potassium ion; and
$\sim$ indicates the attached group can be in either the α or β configuration.

8. A process according to claim 7 where the C$_3$-protected 17-keto steroid (I) and α-metallo-β-metalloxy propionitrile (V) are contacted in a temperature range of about −20° to about −80°.

9. A process according to claim 7 which is performed under anhydrous conditions.

10. A process according to claim 7 where the α-metallo-β-metalloxy propionitrile (V) is dilithio-3-hydroxypropionitrile.

11. A process according to claim 7 where the C$_3$-protected 17-keto steroid (I) is 3-hydroxy-3,5,9(11)-trien-17-one 3-methyl enol ether.

12. A process for the prepration of a corticoid of the formula

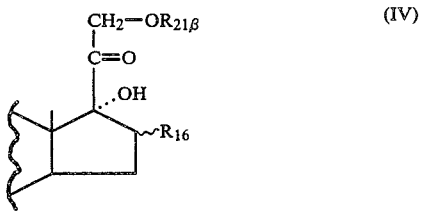

which comprises
(1) contacting a C$_3$ protected 17-keto steroid of the formula

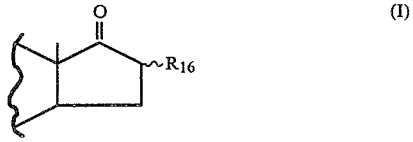

with a α-metallo-β-metalloxypropionitrile of the formula

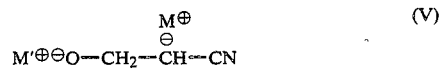

to produce a 17β-hydroxy steroid of the formula

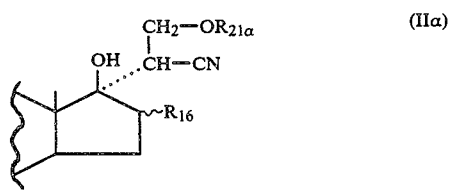

(2) contacting the 17β-hydroxy steroid (II) of step (1) with an acylating or silylating agent to produce a 21-hydroxy protected steroid of the formula

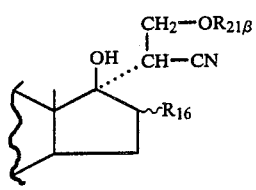

(3) contacting the 21-hydroxy protected steroid (IIβ) of step (2) with a dehydrating agent to produce a $\Delta^{17(20)}$-20-cyano steroid of the formula

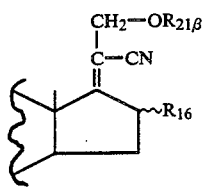

and (4) contacting the $\Delta^{17(20)}$-20-cyano steroid (III) of step (3) with an oxidizing agent where R is alkyl of 1 thru 6 carbon atoms or phenyl;
R' is alkyl of 1 thru 6 carbon atoms or phenyl;
R" is alkyl of 1 thru 6 carbon atoms or phenyl;
$R_{16}$ is a hydrogen atom or methyl group;
$R_{21}\alpha$ is a hydrogen atom or M';
$R_{21}\beta$ is a —$COR_{21}'$ or —$SiRR'R''$ group;
$R_{21}'$ is alkyl of 1 thru 5 carbon atoms or phenyl;
M is a lithium, sodium or potassium ion;
M' is a lithium, sodium or potassium ion;
~ indicates the attached group can be in either the α or β configuration.

13. A process according to claim 12 where the $C_3$-protected 17-keto steroid (I) and α-metallo-β-metalloxy propionitrile are contacted in a temperature range of about $-20°$ to about $-80°$.

14. A process according to claim 12 which is performed under anhydrous conditions.

15. A process according to claim 12 where the α-metallo-β-metalloxy propionitrile (V) is dilithio-3-hydroxypropionitrile.

16. A process according to claim 12 where the $C_3$-protected 17-keto steroid (I) is 3-hydroxy-3,5,9(11)-trien-17-one 3-methyl enol ether.

17. A process according to claim 12 where the dehydrating agent is selected from the group consisting of thionyl chloride, phosphorous oxychloride or chlorosulfonic acid.

18. A process according to claim 12 where the oxidizing agent is selected from the group consisting of potassium permanganate or osmium tetroxide.

* * * * *